(12) United States Patent
Burke et al.

(10) Patent No.: US 6,977,172 B2
(45) Date of Patent: Dec. 20, 2005

(54) METHOD AND APPARATUS FOR TARGETING LOCALIZED ELECTROPORATION

(75) Inventors: Robert D. Burke, Victoria (CA); Ross L. Atkins, Victoria (CA); Diana Wang, Victoria (CA)

(73) Assignee: Innovation and Development Corporation, Victoria (CA)

(*) Notice: Subject to any disclaimer, the term of this patent is extended or adjusted under 35 U.S.C. 154(b) by 308 days.

(21) Appl. No.: 10/179,795

(22) Filed: Jun. 24, 2002

(65) Prior Publication Data

US 2003/0017598 A1 Jan. 23, 2003

Related U.S. Application Data

(63) Continuation of application No. PCT/CA00/01561, filed on Dec. 22, 2000.
(60) Provisional application No. 60/171,444, filed on Dec. 22, 1999.

(51) Int. Cl.[7] .......................... C12M 1/42; C12M 3/00; C12M 1/34; C12N 13/00
(52) U.S. Cl. .............. 435/285.2; 435/287.3; 435/288.6; 435/173.6
(58) Field of Search ................... 435/173.6, 285.2, 435/287.3, 288.6

(56) References Cited

U.S. PATENT DOCUMENTS

| | | | | |
|---|---|---|---|---|
| 5,676,646 A | * | 10/1997 | Hofmann et al. | 604/6.11 |
| 5,874,268 A | * | 2/1999 | Meyer | 435/173.6 |
| 6,150,148 A | * | 11/2000 | Nanda et al. | 435/173.6 |
| 6,208,893 B1 | * | 3/2001 | Hofmann | 604/21 |
| 6,521,430 B1 | * | 2/2003 | Orwar et al. | 435/173.6 |
| 2005/0048651 A1 | * | 3/2005 | Ryttsen et al. | 435/459 |

FOREIGN PATENT DOCUMENTS

WO   WO 99/24110   * 5/1999  ............ A61N 1/32

OTHER PUBLICATIONS

Muramatsu et al. Comparison of Three Nonviral Transfection Methods for Foreign Gene Expression in Early Chicken Embryos in Ovo. 1997. Biochem Biophys Res Comm. vol. 230, pp. 376-380.*

Momose et al. Efficient targeting of gene expression in chick embryos by microelectroporation. Dev. Growth Differ. Jun. 1999. vol 41. No. 3. pp. 335-344.*

Nicholson. Ion-selective microelectrodes and diffusion measurements as tools to explore the brain cell microenvironment. J Neurosci Methods Jul. 1993, vol. 48. No. 3, pp. 199-213.*

Jahaveri et al. Single-unit pH-sensitive double-barreled microelectrodes for extracellurar use. J Appl Physiol. Sep. 1984, vol. 57. No. 3, pp. 907-912.*

Muramatsu et al. Live Detection of the Firefly Luciferase Gene Expression by Bioluminescence in Incubating Chicken Embryos. Anim Sci Technol (Jpn) 1996. vol. 67. No. 10, pp. 906-999.*

Web page entitled 'Electrode—Definition'. Address: http://www.hyperdictionary.com/dictionary/electrode. Accessed online Nov. 8, 2004. pp. 1-2.*

* cited by examiner

*Primary Examiner*—Christopher R Tate
*Assistant Examiner*—Marcela M Cordero Garcia
(74) *Attorney, Agent, or Firm*—Klarquist Sparkman, LLP; Robert H. Barrigar

(57) ABSTRACT

The invention comprises an apparatus and a method of effecting localized electroporation in a relatively small target area and for introducing foreign matter into cellular material in which the target area is located. The cellular material may be in vitro, in ovo or in vivo.

11 Claims, 5 Drawing Sheets

METHOD AND APPARATUS FOR TARGETING LOCALIZED ELECTROPORATION

Figure 1:
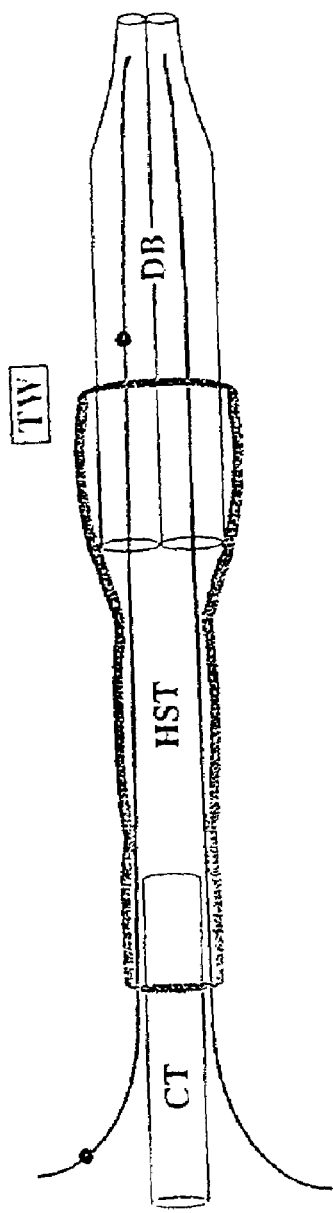

This is a continuation of International Application No. PCT/CA00/01561, filed Dec. 22, 2000, which claims the benefit of U.S. Provisional Application No. 60/171,444, filed Dec. 22, 1999, each of which applications is incorporated herein by reference.

FIELD OF THE INVENTION

This invention relates to the fields of introduction of foreign compounds into cells by electroporation.

BACKGROUND OF THE INVENTION

Current transgenic methods include viral techniques, lipofection, microparticle bombardment, and paddle electroporation (Leber et. al 1996; Methods Cell Biol. 51: 161–83; Muramatsu et. al 1997; Bioc Biophys Res Comm. 23: 376–80). Electroporation is a versatile and popular method of transfecting cells by briefly subjecting them to an electric field, which forms pores in the lipid bilayer, and allows entry of compounds into the cytoplasm (Lurquin 1997; Mol Biotechnol. 7 (1): 5–35). Electroporation overcomes the disadvantages of viral techniques, such as small insert size and biohazard concerns (Leber et. al 1996; Methods Cell Biol. 51: 161–83). Additionally, electroporation has been shown to be more efficient than other methods of in ovo transfection, such as lipofection or microparticle bombardment (Muramatsu et. al 1997; Bioc Biophys Res Comm. 23: 376–80). However, previous electroporation efforts have had a number of limitations, including the inability to effectively target the electroporation, lack of reproducibility of results, and exposure of non-targeted cells to potentially damaging current. Specifically, the electroporation apparatuses of the prior art are generally paddle-like pairs of electrodes, having inherent limitations as to how small a target area would be electroporated and lacking integral means for introducing the foreign matter (commonly DNA) into the cells. Instead, the prior art teaches separate injection of the foreign matter into a localised target area, and electroporation of a larger region including and extending beyond the target area. Accordingly, the prior art teaches unnecessary electroporation of (and thereby potential attendant injury to) cells outside the target area.

Moreover, methods of electroporation in the prior art have proved inefficient and unreliable in localising to any degree the transfection events, and cannot target a specific region of an organ or tissue. Truly localised electroporation could neither be accomplished with prior methods, nor was it contemplated. Prior art methods of in ovo electroporation have involved subjecting the entire embryo to potentially damaging current and the effects have been difficult to reproduce. Although prior art in vivo efforts have included attempts to target on particular organs or tissues, these efforts have involved the injection of a DNA-containing solution into an organ or into the blood stream of an organism and the use of paddle-like pairs of electrodes for the application of the electric field. Cells and tissues subjected to these prior art methods would be not be uniformly electroporated, and as a result only random transfection events would occur within the selected areas. Introduction of foreign compounds other than genetic material by electroporation has likewise suffered from a high degree of unpredictability, due to the inefficiency and unreliability of prior art methods of electroporation.

SUMMARY OF THE INVENTION

The invention comprises methods and apparatus for targeting localised electroporation. In one aspect of the invention, an electroporation apparatus is provided, comprising a fluid delivery means, an electrode means for establishing an electrical field in the target area, and a means for connecting the electrode means to a source of electricity. In preferred embodiments of the inventive apparatus, the electrode means may comprise a pair of conductors. The fluid delivery means has an upstream end, a downstream end, and a passageway fluidly connecting these ends. The upstream end has a receiving aperture for receiving a fluid, and the downstream end comprises a discharging aperture for discharging the fluid into a target area. The electrode means is located at least in part in the vicinity of the discharging aperture of the fluid delivery means. Although the electrode means may generally be located outside the fluid delivery means, in preferred embodiments, substantially the entire electrode means may be located within the fluid delivery means. Accordingly, the apparatus of the invention differs from those of the prior art in that the former has a fluid delivery means integrally associated with the electrode means.

In further preferred embodiments of the inventive apparatus, the following features may be present:
  means for controlling electroporation parameters, such as wave form, number of trains, train duration, train polarity, pulse length, output voltage, and pulse frequency;
  insulation of the electrode means, except at the portions of the electrode means that are in the vicinity of the discharging aperture;
  a fluid source, such as the screw-drive syringe of Example 1 of the Detailed Description, connected upstream to the fluid delivery means.

In at least one preferred embodiment of the apparatus, a double-barreled tube is used both to maintain the conductors spaced apart from one another and to deliver the fluid to the target area.

The inventive apparatus may be used to both electroporate and apply foreign matter to a target area having a diameter of at least as low as 100 $\mu$m.

Where the target area is separated from the outer surface of an organism by intervening matter (such as, for example, skin or some integumentary matter), the apparatus may advantageously be provided with a means for piercing through such intervening matter. Preferably, either the electrode means or the downstream end of the fluid delivery means is sharpened in order to be used to pierce the intervening matter. On the other hand, where the target area is at or near the surface of the organism, the surface downstream end of the fluid delivery means may preferably be polished smooth, so as to minimise the invasiveness of the electroporation.

Another preferred modification of the inventive apparatus is to provide it with means to maintain fluid-mediated contact between the electrode means and the target area, thereby obviating the need for direct physical contact between the apparatus and the target area. This may advantageously be accomplished by, as in the example provided in the Detailed Description, providing the apparatus with a screw-drive syringe, which may both release the fluid into the fluid delivery means and provide a suction to maintain fluid-mediated contact between the electrode means and the target area.

The apparatus of the present invention may provide yet another advantage over the apparatuses of the prior art. The electrode means of the prior art contact the target area, which may lead to greater cellular injury at the point of contact than would occur if the electrode means did not contact the target area. In the present invention, the electrode means need not contact the target area; instead, the ends of the electrode means may be located upstream of the discharging aperture, such that the target area, if it were to come into contact with the inventive apparatus at all, would come into contact only with the discharging aperture. Furthermore, the need for any contact between the inventive apparatus and the target area may be obviated entirely by the presence of a sufficient quantity of electrolyte, which may either be provided through the discharging aperture of the inventive apparatus or may already present in the target area. In this connection, the apparatus may advantageously be provided with a fluid source for providing an electrolyte as well as the foreign matter to be introduced into the target area. Alternatively, the apparatus may be provided with a separate electrolyte source fluidly connected to the fluid delivery means, upstream from the discharging aperture.

Another aspect of the invention is a method for introducing foreign matter into living cellular material. The inventive method comprises selecting a target area, applying the foreign matter to the target area, and electroporating the target area. In contrast to the prior art, the method is characterised in that both the electroporation and the application of the foreign matter are substantially localised to the target area, thereby minimising electroporation injury to non-target cellular material. The target area has a diameter preferably no greater than about 0.5 mm, more preferably no greater than about 100 $\mu$m, and most preferably even less than about 100 $\mu$m. The target area may be located in ovo, in vivo, or in vitro, although clearly the biggest advantage provided by the invention is its suitability to in vivo and in ovo target areas. Moreover, it is far less invasive and with far lower potential for injury than prior art methods of in vivo and in ovo electroporation.

In the context of the target area in ovo, the inventive method preferably further comprises, as a step preceding the electroporation and application of foreign matter, creating an aperture in the covering surrounding the cellular material. Similarly, where the in vivo target area is separated from an outer surface of the organism by some intervening matter, such as, for example, skin, the method preferably comprises, as a step preceding the electroporation and foreign matter application, piercing or creating an aperture in the intervening matter.

The foreign matter introduced into the cellular material in accordance with the invention can be selected from, but is not restricted to, the class comprising polynucleotides, polypeptides, lipids, immunogenic molecules, and so forth. Where the selected target area is located in an organism having an operational immune system, the selection of immunogenic molecules, preferably polynucleotides encoding either antigens, epitopic regions on immunogenic proteins, or immunogenic proteins (or polypeptides comprising either antigens, epitopic regions on immunogenic proteins, or immunogenic proteins) for introduction into the target area by the invention results in an immune response. In this connection, the target area may be selected from the class comprising tissues having associated immune system components, most preferably from the class comprising dermal, epidermal, and mucosal tissues. In this manner, the invention provides a highly efficient, effective, and relatively non-invasive means of immunisation. Where the selected foreign matter comprises immunogenic polynucleotides, the invention provides the additional benefit of savings in time, effort, and cost associated with expression and purification of the counterpart immunogenic proteins.

In respect of all aspects of the invention, the inventors have found that electroporation may be optimised in various respects (such as optimisation of transfection in the target area and minimisation of cellular damage) by controlling electroporation parameters. These parameters include, but are not restricted to, wave form, number of trains, train duration, train polarity, output voltage, and pulse frequency. Regarding the first listed parameter, wave form, there has been some controversy in the prior art as to whether the "square wave" form is the most suitable for electroporation, which it may have been for the prior art methods and apparatuses. However, the inventors have found that other wave forms, such as the "radio frequency pulse" form, appear to be just as well-suited to the present invention as the "square wave" form. In general, it is to be understood that an empirical approach is to be taken.

This invention overcomes drawbacks of viral techniques, lipofection, and previous attempts at in ovo electroporation, and, in doing so, may be advantageously employed in many contexts. For instance, it is of great utility to biologists interested in development or cellular studies of cell lineage, cell fate determination, gene function, especially studies of gene function involving mosaic analysis. It provides the first efficient and reliable method and apparatus for targeting localised electroporation in vivo, and so can be used as a relatively non-invasive, efficient, and effective means of DNA immunisation, as a platform for gene therapeutics, and for many other applications.

SUMMARY OF THE DIAGRAMS

FIG. 1. Schematic drawing of the double-barreled suction electrode (not to scale). TW: tungsten wire, CT: capillary tube mounting shaft, HST: heat shrink tubing, DB: double-barreled capillary tube drawn and forged.

Figure 2:
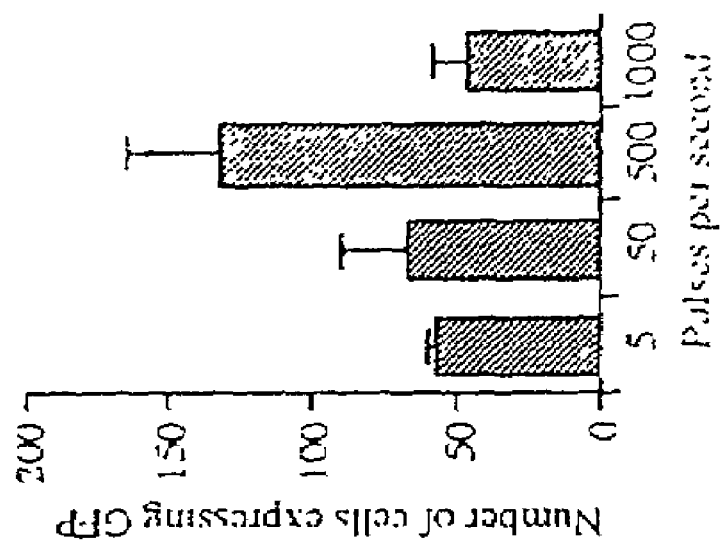

FIG. 2. The effect of varying pulse frequency on mean number of avian embryo cells transfected. Six, one-second trains were administered and pulse length was adjusted to provide equal power output. Electrodes were approximately the same size and 2–5 embryos were analysed per condition. Bars indicate standard errors.

Figure 3:
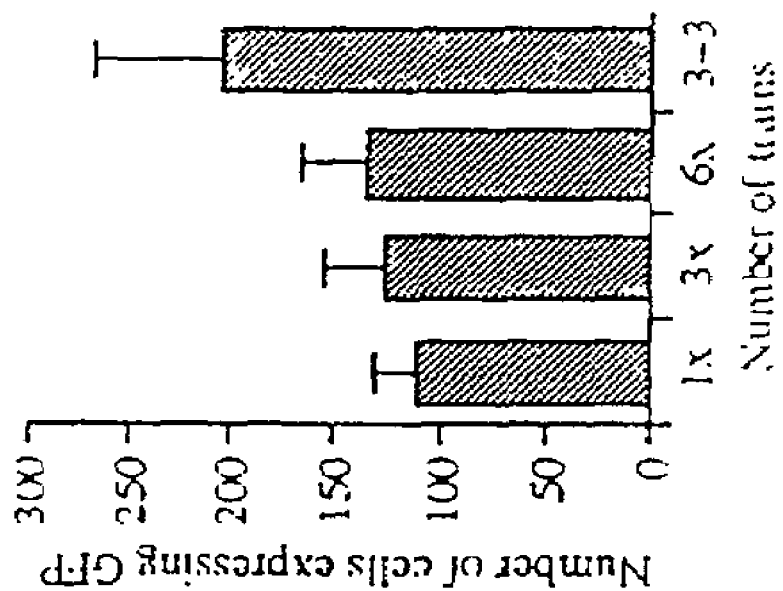

FIG. 3. The effect of train number and polarity on mean number of avian embryo cells transfected. Trains were one second long and alternating train polarity is indicated by 3+3. All tests were performed at 500 pulses per second with a pulse duration of 1 ms. Electrodes were approximately the same size and 2–5 embryos were analysed per condition. Bars indicate standard errors.

Figure 4:
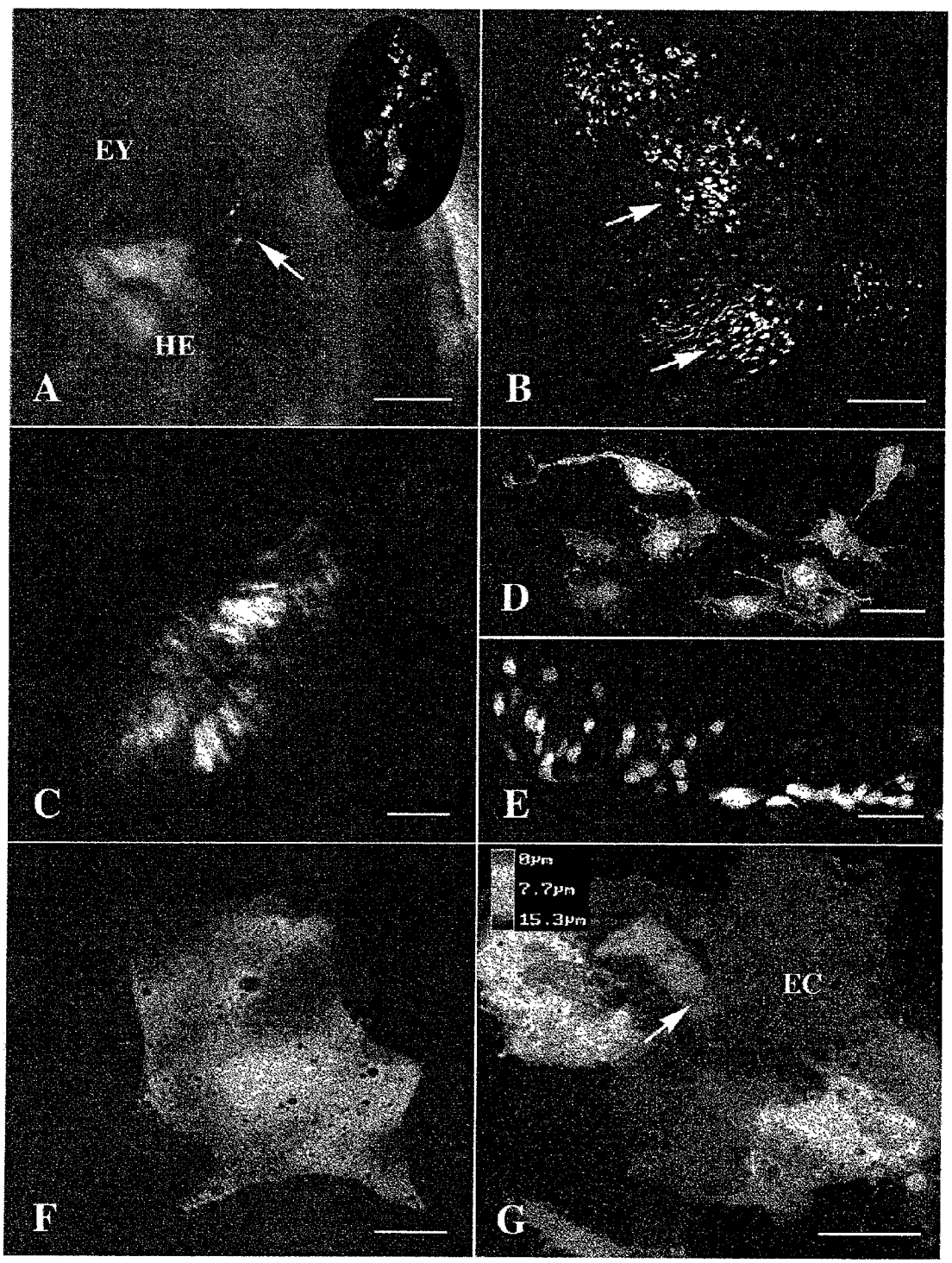

FIG. 4. Whole mount chicken embryos showing GFP-expressing cells 48 hours post-electroporation. (A) Left side of head of embryo in which rhombomeric neural crest was targeted. GFP-expressing neural crest cells have migrated ventrally and are visible in the first branchial arch (Arrow). Inset shows magnified view of fluorescent cells. EY: eye, HE: heart, Bar: 500 $\mu$m. (B) Confocal laser scanning image of dorsal head region of embryo after train polarity alternation. Arrows indicate barrel locations. Bar: 200 $\mu$m. (C) GFP expression in cells comprising half the lens vesicle of an embryo in which presumptive lens epithelium was electroporated. Bar: 50 $\mu$m. (D) Confocal image of cells within the neural tube expressing GFP after neural plate was electroporated. Bar: 25 μm. (E) Confocal image of GFP-expressing cells migrating from cranial neural folds. The movement of these cells away from the neural tube suggest they are neural crest derived. Bar: 50 μm. (F) Confocal image of an epithelial cell showing cytoplasmic GFP expression. Bar: 10 μm. (G) Depth coding constructed from a confocal stack showing epithelial cells and cells up to 15 μm below the point of transfection expressing GFP. EC: epithelial cells, Arrow: deep cell, Bar: 25 μm.

Figure 5:
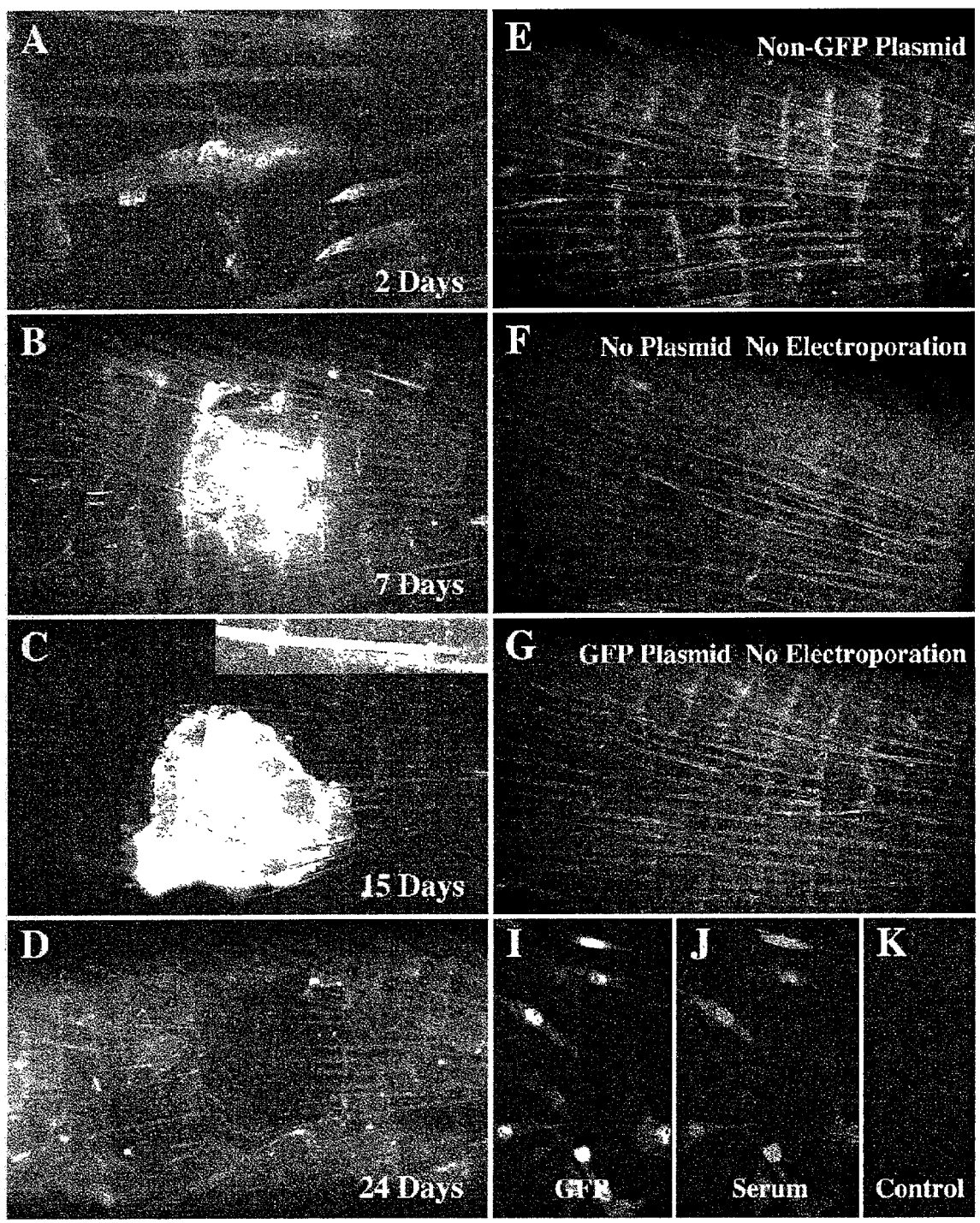

FIG. 5. Fluorescent images of localised electroporation of mouse tail. (A) Spot 2 days after electroporation (200V). (B) 7 days, the spot is larger and fluorescence is beneath the surface. (C) 15 days after electroporation, the cells expressing GFP formed a small, well demarked spot at the surface of the skin. Inset shows one of several hairs that were brightly fluorescent. (D) After 24 days, the cells expressing GFP appear to have been sloughed. (E) Control preparation in which a control plasmid, incapable of mammalian expression was transfected. (F) Control in which a spot was only pierced with the electrode, no plasmid was used and no electroporation was done. (G) Spot in which GFP expression plasmid was released into an incision, but not electroporated. (H) Avian cells expressing GFP. (I) The same cells prepared for immunofluorescence with serum harvested after localised electroporation. (J) Control in which cells serum was used with cells not expressing GFP to determine background immunoreactivity.

DETAILED DESCRIPTION OF THE INVENTION

The method of this invention is in principle applicable to all multicellular organisms and cultures of unicellular organisms, but it is to be understood that where species selected are different from those mentioned in the following examples, an empirical approach to selection of wave form, number of trains, train duration, train polarity, pulse frequency, pulse length, and output voltage is recommended, preferably with a view to optimising electroporation while minimising cellular damage. A variety of capillary tubes, mounting shafts, conductors, and other components are suitable for constructing the inventive apparatus so the particular choice is not expected to be important.

EXAMPLE 1

Electroporation of Avian Embryos

An electroporation apparatus, back-filled with DNA containing solution and driven by a conventional neurophysiological stimulator, was used to transfect plasmids containing green-fluorescent protein (GFP) into avian embryos. The electroporation apparatus was made from a 1.2 mm×0.6 mm, 4 inch, double-barrelled glass capillary tube (catalog #6070, A-M Systems) which was drawn on a vertical pipette puller (Model 700C, David Kopf Instruments), broken back to an inside diameter of 200–250 μm, and forged. Tungsten wire (catalog #7960, A-M Systems). coated with Teflon as an insulator and with the Teflon removed 5 mm from the ends, was inserted in each barrel to within 1 mm of the tip. A capillary tube mounting shaft was attached with heat-shrink tubing and sealed with epoxy (FIG. 1). This apparatus was connected with polyethylene tubing to a screw-drive syringe, and was held in a micromanipulator. The tungsten wire leads were connected to the poles of a stimulus isolation unit attached to a square wave stimulator (Grass S48).

Plasmid (eGFP NI, Clontech) was diluted to 250 ng/μl in 0.85 M NaCl. The double-barreled capillary tube was back-filled with DNA solution and positioned in contact with the surface of the embryo. Fertile chicken eggs (stage 10–13) were windowed and the vitelline layer over the target area was carefully reflected with a fine tungsten needle (1,5). A seal was formed by applying a small amount of suction to the tube with the screw-drive syringe. One-second trains of pulses were delivered and pulse frequency, pulse length, train number, and train polarity were varied as required. Train length was always one second and a reciprocal relationship was maintained between the pulse frequency and pulse length, thus delivering identical total power at each setting. The voltage output of the stimulator was adjusted to the maximum setting that did not cause visible tissue damage. This differed slightly for each apparatus, but generally was between 70 and 80 V. Immediately after administration of the electroporation trains, the apparatus was backed slightly away from the embryo, the suction released, and a small volume of DNA solution was injected over the embryo. The egg was resealed with adhesive tape and returned to the incubator for 48 hours. Whole embryos were removed into phosphate buffered saline (PBS) and the amnion was removed. GFP-expressing cells were visualised using either an epifluorescent compound microscope (Zeiss) or a confocal laser scanning microscope (Zeiss). If fixation was required, 2% paraformaldehyde in PBS for 5 min proved to be adequate without inducing auto-fluorescence.

Electroporation produced two scattered patches of GFP-expressing cells at the point of electroporation. Patch diameter exceeded conductor size but was approximately proportional to it. The patch associated with the negative pole of the electrode means normally contained the majority of GFP-expressing cells; however, with alternating train polarities, both patches were similar in size. This is consistent with observations of paddle electroporation producing transfected cells on the side of the neural tube nearest the positive paddle—in both cases DNA follows a cathode to anode path. Early GFP expression was visible less than two hours post-electroporation, but did not reach maximum intensity until 24 to 48 hours. Expression continued until incubation was halted (>8 days), at which point thousands of transfected cells were present. GFP intensity was slightly lower which is consistent with episomal plasmid dilution through mitotic division.

Increasing the number of trains provided an apparent increase in transfection efficiency (FIG. 3), with no decrease in survivorship. Alternating the polarity between trains increased the average number of cells transfected from 230 to almost 400, though a total of six trains was delivered in each case. Six alternating trains were significantly more efficient than a single train ($P<0.01$).

Five hundred pulses per second (pulse length 1 ms) produced the optimal number of transfected cells (FIG. 2). Higher and lower frequencies resulted in approximately half the number of transfected cells. Transfection rates at the lowest frequency (5 pulses per second) with long pulse durations (100 ms) decreased survivorship and increased the incidence of abnormal embryos. No deformities were observed at high pulse frequencies (low pulse duration).

Given the number of variables in electroporation systems, the above parameters may require modification when the electroporation apparatus is adapted to different power sources or situations. For instance, when titrating the voltage, it is advisable to find the threshold at which scarring occurs and then decrease output by 10–20V.

Multiple cell types and various targets were controllably electroporated. Migration was not impeded and cells proceeded on predicted routes (FIG. 4a). Hundreds of cells could be transfected with large barrel diameters and alternating train polarity (FIG. 4b). Cells of the lens vesicle (FIG. 4c), neuronal cells (FIG. 4d), neural crest cells (FIG. 4e), and epithelial cells (FIG. 4f), were successfully transfected. Surface epithelial cells and mesenchyme deep to the point of electroporation expressed GFP (FIG. 4g), indicating that direct contact with electrode is not necessary.

EXAMPLE 2

In Vivo Mammalian Electroporation

The electroporation apparatus was made from a 1.2 mm×0.68 mm, 4 inch, double-barrelled borosilicate glass capillary tube (catalog #6350, A-M Systems) which was drawn on a vertical pipette puller (Model 700C, David Kopf Instruments), broken back to and ground to a bevel edge with a Narashige EG-4 electrode grinder. Teflon-coated tungsten wire (catalog #7960, A-M Systems), with the Teflon removed 5 mm from the ends, was inserted in each barrel to within 1 mm of the tip. A capillary tube mounting shaft (catalog #6260, A-M Systems) was attached with heat-shrink tubing and sealed with hotmelt glue. The apparatus was held in a micromanipulator and connected with polyethylene tubing to a screw-drive syringe. The tungsten wire leads were connected to the poles of a BioRad Gene Pulser II with RF Module.

Plasmid (eGFP N1, Clontech) was diluted to 250 ng/$\mu$l in 0.85 M NaCl. Female Balb/C mice were restrained in a tube restraining device and their tails taped to the base. The tails were swabbed with ethanol and marked with an indelible pen. The double-barrelled tube was backfilled with DNA solution and the skin of the mouse's tail was pierced. A small pool of DNA solution was released and electroporated. Electroporations consisted of 10, 40 msec bursts at 30 KHz and bursts were 0.2 sec apart with either 200, 300 or 400 Volts. The train polarity was then reversed and a second set of pulses applied. Immediately after administration of the electroporation trains, the apparatus was backed slightly away, and a small volume of DNA solution was released. Sterile water was used to rinse the electrode to prevent clogging and prolong its life. Mice were returned to the cage and examined at intervals with a Leica MZ Apo microscope fitted with a GFP module.

Serum was collected 23 days after electroporation and used in an indirect immunofluorescence assay with cells transfected with a GFP expression vector.

Results and Discussion

After 48 hours the small incision that was electroporated had a slight green fluorescence that was distinguishable from the background fluorescence (FIG. 1A). After 1 week the spot that had been electroporated appeared slightly swollen and inflamed. With fluorescence microscopy, there was a bright fluorescent region with diffuse boundaries beneath the surface of the tail (FIG. 1B). At 15 days there was a small, colourless scab at the point of electroporation. There was a well-demarked spot of fluorescence, and in some mice, there were hairs adjacent to the site of transfection that were brightly fluorescent throughout their length (FIG. 1C). By 24 days, the inflammation had subsided and there was a slightly pink, hairless spot at the site of transfection.

In control preparations in which a non-expression plasmid was electroporated, or a sham site in which there was no plasmid and no electroporation, or a site at which plasmid was released without electroporation, the site had healed over within 7 days and no inflammation, nor fluorescence was detected (FIGS. 1E, F, G). In all of the voltages attempted there were fluorescent cells, and there did not appear to be any differences in the size of the region expressing GFP.

These experiments indicate that localised electroporation can be applied to mammals. The use of the suction apparatus on the surface of the skin was not successful, probably because the skin forms an effective barrier to the aqueous DNA solution. However, once the skin is broken, a small region of cells at the point of electroporation express the GFP reporter gene. The observation of hairs expressing GFP suggests that the cells of the hair follicle that proliferate to form the hair shaft were transfected in some instances. The size of the fluorescent spot produced did not appear to correlate with the voltage used, suggesting all were above the threshold required for efficient transfection.

As there appeared to be a localised inflammatory response to the transfection, the immune response of the mice to the GFP reporter protein was assayed. A sample of blood was obtained from a transfected mouse and serum was used in an indirect immunofluorescence assay of avian cells transfected with a GFP expression plasmid. The cells that express GFP are also immunoreactive to the serum, indicating the presence of antibodies to GFP (FIG. 1H, I). Controls included normal mouse serum or cells sham transfected and neither contained cells that were immunoreactive (FIG. 1J).

These experiments indicate that mice can be immunised by localised electroporation. Cells at the site of electroporation express the transgene for about 3 weeks, and then appear to be sloughed from the skin. This invention has considerable potential for use by researchers. There is saving in time and effort if mice can be immunised with DNA encoding a protein of interest There is no need to express and purify the protein as an immunogen. The fact that mice express the transgene for only a few weeks, means that this method of immunisation could, after safety tests, be used for immunisation of livestock, pets and potentially humans. The localised electroporation apparatus provides a relatively non-invasive means of DNA immunisation. In addition localised electroporation may also function as a platform for gene therapeutics, including for example transient gene therapeutics. There are situations where expression of a transgene ectopically in skin cells for a short period of time would be useful.

References

1. Hamburger, V., & Hamilton, H. L. 1951. A series of normal stages in the development of the chick embryo. J Morph. 88: 49–92
2. Leber, S. M., Yamagata, M., & Sanes, J. R. 1996. Gene transfer using replication-defective retroviral and adenoviral vectors. Methods Cell Biol. 51: 161–83
3. Lurquin, P. F. 1997. Gene transfer by electroporation. Mol Biotechnol. 7 (1): 5–35
4. Muramatsu, T., Mizuntani, Y., Ohmori, Y., & Okumura, J. 1997. Comparison of three nonviral transfection methods for foreign gene expression in early chicken embryos in ovo. Bioc Biophys Res Comm. 23: 376–80
5. Selleck, M. A. 1996. Culture and microsurgical manipulation of the early avian embryo. Methods Cell Biol 51: 1–21

The embodiments of the invention in which an exclusive property or privilege is claimed are defined as follows:

1. An electroporation apparatus, comprising a fluid deliverer comprising a double-barrelled tube having an upstream end, a downstream end, and a passageway fluidly connecting said ends, wherein the upstream end comprises a receiving aperture for receiving a fluid, and the downstream end comprises a discharging aperture for discharging the fluid into a target area;

an electrode for establishing an electrical field in the target area, the electrode being located at least in part in the vicinity of the discharging aperture, wherein the electrode comprises a pair of conductors separated by a spacer; and a connector for connecting the electrode to an electrical source.

2. The apparatus of claim 1, wherein the downstream end of the fluid deliverer comprises a substantially smooth surface.

3. The apparatus of claim 1, wherein the downstream end of the fluid deliverer comprises a piercing means.

4. The apparatus of claim 1, further comprising a fluid source fluidly connecting with the receiving aperture.

5. The apparatus of claim 4, wherein the fluid source comprises a fluid-containing syringe.

6. An integrated electroporation apparatus, comprising:

a fluid deliverer having an upstream end, a downstream end, and a passageway fluidly connecting said upstream end to said downstream end, wherein the upstream end comprises a receiving aperture for receiving a fluid, and the downstream end comprises a discharging aperture for discharging the fluid onto a target area of a target tissue;

an electrode for electrical communication with the target tissue for establishing an electrical field in the target tissue, the electrode proximate to and integral with said fluid deliverer and spaced from said discharge aperture, to separate said electrode from the target tissue, wherein the electrode comprises a pair of conductors and wherein the electrode is located substantially within the fluid deliverer;

a spacer physically separating the conductors, wherein the fluid deliverer comprises the spacer, and wherein the spacer comprise a double-barrelled tube and wherein one of each conductor is located within one of each barrel;

a controller for at least one electroporation parameter, wherein the electroporation parameter is selected from the class comprising wave form, number of trains, train duration, train polarity, pulse length, output voltage, and pulse frequency;

an insulator insulating a portion of the electrode, wherein at least a portion of the electrode in the vicinity of the discharging aperture is not insulated; and a connector for connecting the electrode to an electrical source.

7. The apparatus of claim 6, wherein the fluid deliverer comprises the double-barrelled tube.

8. The apparatus of claim 7, wherein the downstream end of the fluid deliverer comprises a substantially smooth surface.

9. The apparatus of claim 7, wherein the downstream end of the fluid deliverer comprises a piercing means.

10. The apparatus of claim 7, further comprising a fluid source fluidly connecting with the receiving aperture.

11. The apparatus of claim 10, wherein the fluid source comprises a fluid-containing syringe.

* * * * *